US012138614B1

(12) United States Patent
Kovo et al.

(10) Patent No.: US 12,138,614 B1
(45) Date of Patent: Nov. 12, 2024

(54) KAOLIN BASED ZEOLITE A FOR RAPID REDUCTION OF POULTRY LITTER ODOR

(71) Applicant: KING FAISAL UNIVERSITY, Al-Ahsa (SA)

(72) Inventors: Abdulsalami Sanni Kovo, Minna (NG); Abdulrazak Jinadu Otaru, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/432,772

(22) Filed: Feb. 5, 2024

(51) Int. Cl.
B01J 20/18 (2006.01)
A61L 11/00 (2006.01)
B01J 20/28 (2006.01)
B01J 20/30 (2006.01)
C01B 39/18 (2006.01)

(52) U.S. Cl.
CPC ............... *B01J 20/18* (2013.01); *A61L 11/00* (2013.01); *B01J 20/28004* (2013.01); *B01J 20/28016* (2013.01); *B01J 20/3071* (2013.01); *B01J 20/3078* (2013.01); *B01J 20/3085* (2013.01); *C01B 39/18* (2013.01); *C01P 2002/72* (2013.01); *C01P 2004/03* (2013.01)

(58) Field of Classification Search
CPC .................. B01J 20/18; B01J 20/28004; B01J 20/28016; B01J 20/3071; B01J 20/3078; B01J 20/3085; A61L 11/00; C01B 39/18
See application file for complete search history.

(56) References Cited

U.S. PATENT DOCUMENTS 5,045,295 A 9/1991 Tannous et al.

FOREIGN PATENT DOCUMENTS

| CN | 1583229 A | 2/2005 |
| CN | 109607729 A | 4/2019 |
| DE | 3013397 A1 | 10/1981 |

OTHER PUBLICATIONS

English Abstract for CN 108190909 (Year: 2018).*

* cited by examiner

*Primary Examiner* — Sean E Conley
(74) *Attorney, Agent, or Firm* — Nath, Goldberg & Meyer; Joshua B. Goldberg

(57) ABSTRACT

A method of forming a zeolite composition for waste treatment is disclosed herein. The method includes refining kaolin to form a metakaolin; mixing the metakaolin with sodium hydroxide (NaOH) to obtain a mixture; aging and heating the mixture; washing the mixture; drying the mixture in a microwave to obtain crystals; and obtaining a zeolite composition.

19 Claims, 3 Drawing Sheets

KAOLIN BASED ZEOLITE A FOR RAPID REDUCTION OF POULTRY LITTER ODOR

BACKGROUND

1. Field

The disclosure of the present patent application relates to a composition and method of waste treatment, and particularly to a composition and method for treating poultry litter, including, but not limited to, deodorizing the waste and/or removing pollutants. The composition could be administered directly to waste, or, for example, to poultry litter.

2. Description of the Related Art

Zeolites can be used for the removal of offensive odors emanating from poultry farms due to poultry litter among other waste material in poultry farms. Poultry litter may include pollutants such as formaldehyde (HCHO), total volatile organic compounds (TVOC), particulate matter having a size of 2.5 microns ($P.M_{2.5}$), particulate matter having a size of 10 microns ($P.M_{10}$), carbon dioxide ($CO_2$) and ammonia ($NH_3$). The reduction of offensive odors can also decrease the attraction of odor loving rodents, flies, and reptiles into the farming areas.

The high cost of production associated with synthesis of Zeolites from analytical grade chemicals (sodium aluminate, sodium metasilicate, and silica gel), has necessitated the exploration of other cheap, readily available sources of alumina and silica to reduce the final cost of synthetic zeolites.

The deodorization of poultry litter has the potential to benefit the animals, the farmers, and the environment by providing a cleaner area for poultry to live in a poultry farm. It would be desirable to synthesize an inexpensive zeolite composition in a cost-effective manner to revolutionize the global farming business.

Thus, a composition and method for waste treatment solving the aforementioned problems is desired.

SUMMARY

Presented herein is a method for efficiently and sustainably processing Zeolite A from Kaolinite raw materials to remove poultry waste odor. The process is novel and is intended to be a modification of the hydrothermal process by which even a low quality kaolin can be transformed into a crystalline Zeolite A. The modification involves fusion of raw kaolin with sodium hydroxide (NaOH) at temperatures ranging between about 550° C. and about 600° C. The fusion may be followed by microwave treatment at a reduced time using a regulated frequency/power regulator. The zeolite A may be confirmed by X-ray diffraction and scanning electron microscope analysis.

A method of forming a zeolite composition for waste treatment is disclosed herein. The method includes refining kaolin to form a metakaolin; mixing the metakaolin with sodium hydroxide (NaOH) to obtain a mixture; aging and heating the mixture; washing the mixture; drying the mixture in a microwave to obtain crystals; and obtaining a zeolite composition.

A method of deodorizing animal waste may include treating animal waste with the synthesized zeolite described herein. The synthesized zeolite may be used to treat poultry litter. The zeolite may be used in a 1% to 15% w/w with poultry litter. The poultry litter may be treated with the zeolite for at least about 10 minutes to at least about 180 minutes. The zeolite may be used to remove pollutants from the poultry litter. The pollutants may include formaldehyde (HCHO), total volatile organic compounds (TVOC), particulate matter, carbon dioxide ($CO_2$), and ammonia ($NH_3$).

These and other features of the present subject matter will become readily apparent upon further review of the following specification.

DETAILED DESCRIPTION OF THE PREFERRED EMBODIMENTS

Figure 1:
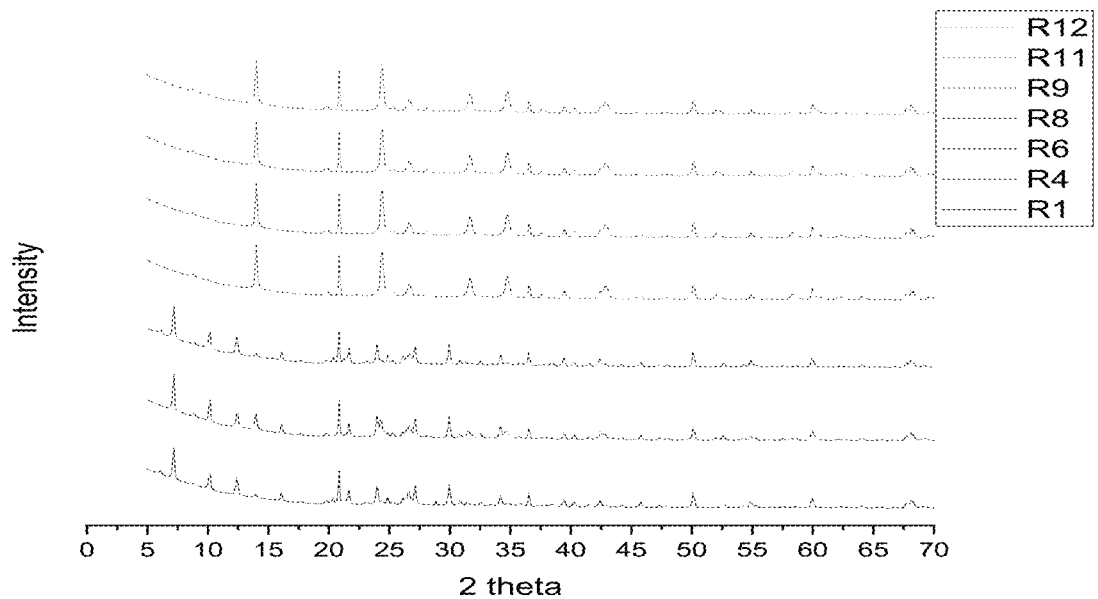
FIG. 1 shows a graph of XRD patterns of embodiments of zeolites prepared as descried herein.
Figure 2A:
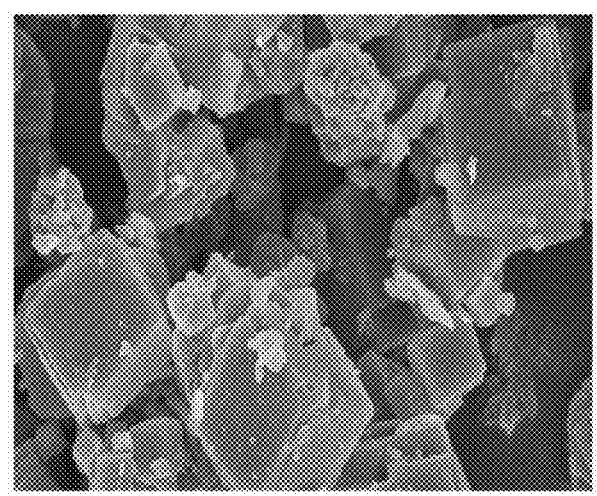
FIGS. 2A, 2B, 2C, and 2D shows SEM images for certain embodiments of zeolites prepared as described herein.
Figure 2B:
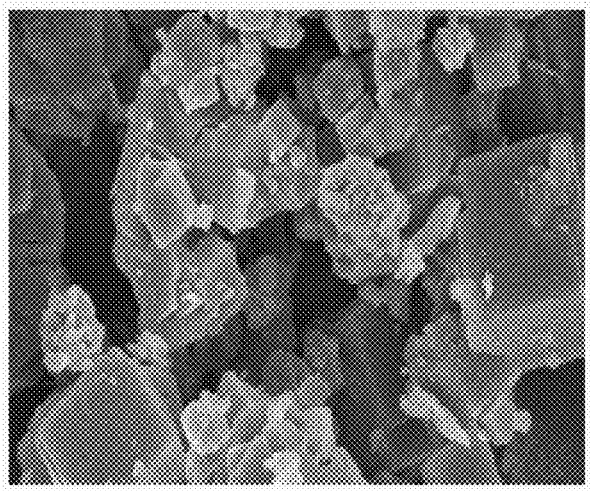
Figure 2C:
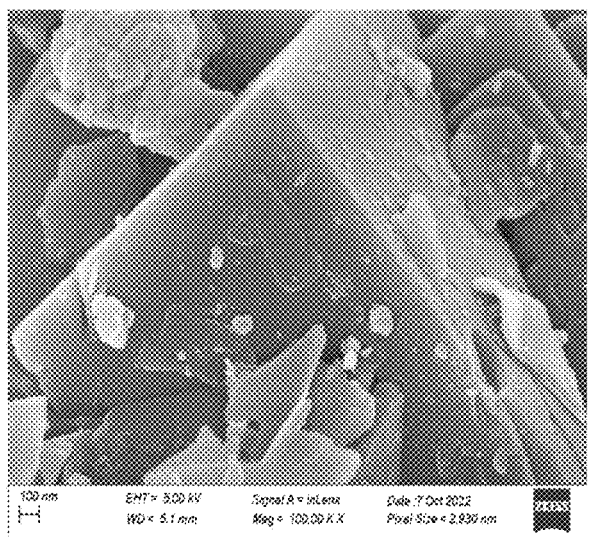
Figure 2D:
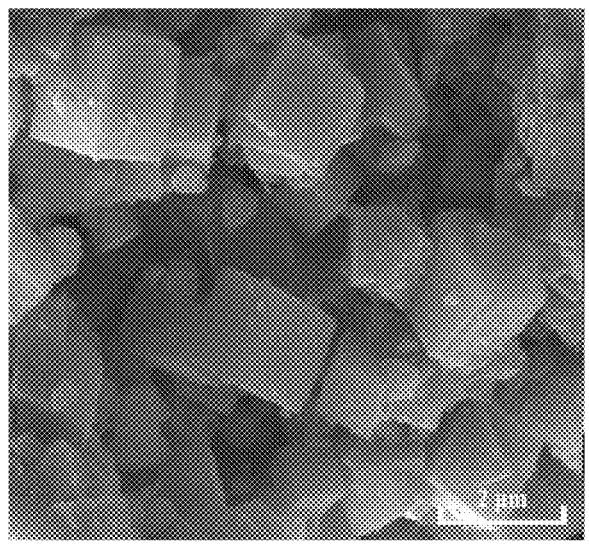

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

A method of forming a zeolite composition for waste treatment as described herein may include refining kaolin to form a metakaolin; mixing the metakaolin with sodium hydroxide (NaOH) to obtain a mixture; aging and heating the mixture; washing the mixture; drying the mixture in a microwave to obtain crystals; and obtaining a zeolite composition.

In various embodiments, the kaolin may include Aloji Nigerian Kaolin. In other embodiments, the kaolin used may be any naturally occurring kaolin. In still other embodiments, the kaolin may be commercially available kaolin.

In some embodiments, the kaolin may be refined at temperatures of about 600° C. to about 850° C., or about 600° C., or about 725° C., or about 850° C.

In further embodiments, the NaOH may have a concentration of about 5 M to about 8 M. In other embodiments, the NaOH may have a concentration of about 6.5 M. In some embodiments, the concentration of NaOH may be referred to as Alkalinity of the solution.

In additional embodiments, the mixture may be stirred with a magnetic stirrer. In some embodiments, the mixture may be stirred for about at least 1 hour to at least about 3 hours, or about 1 hour, about 2 hours, or about 3 hours.

In another embodiment, the mixture may be heated in an autoclave. The autoclave may be a Teflon (Teflon is a registered trademark of Chemours a company headquartered in Wilmington, DE, USA) lined stainless steel coated autoclave. The mixture may be heated at various temperatures in the autoclave.

In further embodiments, the mixture may be dried in a microwave at about 80° C. to about 150° C. The mixture may be dried in the microwave for at least about 8 hours. In still further embodiments, the mixture may be dried in a microwave at about 80° C., about 115° C., or about 150° C.

The present disclosure also relates to method of deodorizing animal waste. The method of deodorizing animal waste may include treating the animal waste with the zeolite described herein. In various embodiments, the zeolite may be added on top of the animal waste. In other embodiments, the zeolite may be mixed with the animal waste. In still other embodiments, the zeolite may be added to waste receptacles to deodorize the animal waste after disposal. The animal waste may include poultry litter. In various embodiments, the zeolite may be used to treat animal waste from other animals, such as, by non-limiting example, rabbits, goats, and other domesticated farm animals.

In further embodiments, the zeolite may be added to the poultry litter in an about 1% w/w to an about 15% w/w ratio. In other embodiments, the zeolite may be added to the poultry litter in an about 1% w/w ratio, an about 5% w/w ratio, an about 10%, w/w ratio, and an about 15% w/w ratio. In various embodiments, the poultry litter may be treated with the zeolite for at least about 10 minutes to at least about 180 minutes. In still other embodiments, the poultry litter may be treated with zeolite for at least about 10 minutes, about 20 minutes, about 30 minutes, about 60 minutes, about 120 minutes, or about 180 minutes.

In other embodiments, the method of deodorizing animal waste may include removing pollutants from the animal waste using zeolite. In various embodiments, the pollutants may include formaldehyde (HCHO), total volatile organic compounds (TVOC), particulate matter, carbon dioxide ($CO_2$), and/or ammonia ($NH_3$). In other embodiments, the animal waste may include other pollutants, such as by non-limiting example, urea, methane and nitrous oxide, hydrogen sulfide and other noisome chemicals. In various embodiments, the particulate matter may have a size of about 2.5 microns to about 10 microns. In still other embodiments, the particulate matter may be about 2.5 microns or about 10 microns.

The following examples illustrate the present teachings.

Example 1

Synthesis of Zeolite A

Zeolite A was synthesized from Aloji Nigerian Kaolin using the conventional hydrothermal method. Refined kaolin was metakolinzed at varying temperatures. The metakaolin obtained were then mixed with different concentration of sodium hydroxide (NaOH) and the resulting mixture was stirred using a magnetic stirrer for varying stirring time. The homogenous solution was aged and then heated in a Teflon lined stainless steel autoclave for 3 h and at varying temperatures. The resultant product obtained was washed and dried in an oven at 100° C. for 8 hours and the crystals obtained stored in an airtight container.

Response Surface Methodology (RSM) with Box-Benken experimental design was used to study the effect of four variables namely metakaolinization temperature, Alkalinity, stirring time and Crystallization temperature was studied. The variables studied and their level are indicated in Tables 1 and 2 below.

TABLE 1

Level of variable for zeolite A synthesis

| Levels | High | Medium | Low |
|---|---|---|---|
| Coding | +1 | 0 | −1 |
| Metakaolinization temperature (° C.) | 850 | 725 | 600 |
| Alkalinity (M) | 8 | 6.5 | 5 |
| Stirring time (h) | 3 | 2 | 1 |
| Crystallization temperature (° C.) | 150 | 115 | 80 |

TABLE 2

Box-Benkhen design matrix for synthesis of zeolite A using hydrothermal method.

| Exp Run | NaOH Concentration (M) | Metakaolinization temperature (° C.) | Stirring Time (h) | Crystallization temperature (° C.) |
|---|---|---|---|---|
| 1 | 6.5 | 725 | 1 | 80 |
| 2 | 6.5 | 725 | 3 | 80 |
| 3 | 5 | 725 | 2 | 80 |
| 4 | 8 | 725 | 2 | 80 |
| 5 | 6.5 | 850 | 2 | 80 |
| 6 | 6.5 | 600 | 2 | 80 |
| 7 | 5 | 725 | 3 | 115 |
| 8 | 5 | 850 | 2 | 115 |
| 9 | 6.5 | 600 | 3 | 115 |
| 10 | 6.5 | 725 | 2 | 115 |
| 11 | 8 | 600 | 2 | 115 |
| 12 | 6.5 | 850 | 3 | 115 |
| 13 | 6.5 | 725 | 2 | 115 |
| 14 | 8 | 850 | 2 | 115 |
| 15 | 8 | 725 | 3 | 115 |
| 16 | 5 | 725 | 1 | 115 |
| 17 | 5 | 600 | 2 | 115 |
| 18 | 6.5 | 725 | 3 | 150 |
| 19 | 6.5 | 725 | 2 | 115 |
| 20 | 8 | 725 | 2 | 150 |
| 21 | 8 | 725 | 1 | 115 |
| 22 | 6.5 | 850 | 2 | 150 |
| 23 | 6.5 | 850 | 1 | 115 |
| 24 | 6.5 | 600 | 2 | 150 |
| 25 | 6.5 | 600 | 1 | 115 |
| 26 | 6.5 | 725 | 2 | 115 |
| 27 | 5 | 725 | 2 | 150 |
| 28 | 6.5 | 725 | 1 | 150 |
| 29 | 6.5 | 725 | 2 | 115 |

The XRD plot obtained from zeolites synthesized during the optimization process is shown in FIG. 1.

The morphology of the synthesized zeolite A was obtained via SEM. The micrographs shown in FIG. 2A-2D depict some well-developed cubic crystals that is typical of zeolite A. Therefore, the micrograph showed an improvement from the original of plate-like hexagonal morphological structure of kaolin surfaces to form euhedral cubic crystals of zeolite A.

Example 2

Deodorization of Poultry Litters

In the deodorization of poultry litter, 5 g of poultry litter was taken as the basis and this was treated with the zeolite that was synthesized. The effect of two factors (time and the mass of adsorbent) were studied. In the study of the effect of mass of zeolite on deodorization of poultry litter, zeolite weight that corresponds to 1%, 5%, 10% and 15% weight of poultry litter was used in deodorization process using various time interval of 10, 20, 30, 60, 120 and 180 minutes. Then an air quality meter was used to measure the rate of removal of certain gases This was done in triplicate to ascertain the liability of the instrument. The variables were studied using a D-optima design as depicted in Table 3.

TABLE 3

D-optima design matrix for deodorization of poultry litter

| Experimental Run | A: time (min) | B: mass of zeolite (g) |
|---|---|---|
| 1 | 60 | 0.05 |
| 2 | 60 | 0.50 |
| 3 | 30 | 0.05 |
| 4 | 30 | 0.75 |
| 5 | 60 | 0.75 |
| 6 | 30 | 0.50 |
| 7 | 20 | 0.75 |
| 8 | 120 | 0.50 |
| 9 | 120 | 0.05 |
| 10 | 120 | 0.75 |
| 11 | 120 | 0.25 |
| 12 | 180 | 0.75 |
| 13 | 60 | 0.25 |
| 14 | 10 | 0.50 |
| 15 | 10 | 0.75 |
| 16 | 10 | 0.25 |
| 17 | 180 | 0.25 |
| 18 | 180 | 0.50 |
| 19 | 20 | 0.50 |
| 20 | 20 | 0.05 |
| 21 | 180 | 0.05 |
| 22 | 20 | 0.25 |
| 23 | 10 | 0.05 |
| 24 | 30 | 0.05 |

Example 3

Deodourization of Poultry Litter

The Table 4 gives the experimental design result for the deodorization of poultry litter. The response which is the concentration of pollutant was measured for the amount of HCHO (formaldehyde), TVOC (total volatile organic compounds), $P.M_{2.5}$ (particulate matter 2.5 microns), $P.M_{10}$ (particulate matter 10 microns), $CO_2$ (carbon dioxide) and Ammonia ($NH_3$).

TABLE 4

Results for Deodorization of poultry litter

| RUN | Time (mins) | Mass of Zeolite (g) | HCHO (mg/m³) | TVOC (mg/m³) | $PM_{2.5}$ (ug/m³) | $PM_{10}$ (ug/m³) | $CO_2$ (ppm) |
|---|---|---|---|---|---|---|---|
| 1 | 60 | 0.05 | 0.529 | 3.961 | 9 | 14 | 553 |
| 2 | 60 | 0.50 | 0.415 | 3.045 | 3 | 9 | 374 |
| 3 | 30 | 0.05 | 0.539 | 4.192 | 10 | 16 | 593 |
| 4 | 30 | 0.75 | 0.462 | 3.402 | 8 | 12 | 437 |
| 5 | 60 | 0.75 | 0.423 | 2.797 | 7 | 13 | 349 |
| 6 | 30 | 0.50 | 0.477 | 3.247 | 3 | 14 | 425 |
| 7 | 20 | 0.75 | 0.494 | 3.701 | 7 | 9 | 461 |
| 8 | 120 | 0.50 | 0.351 | 1.786 | 0 | 4 | 306 |
| 9 | 120 | 0.05 | 0.518 | 3.946 | 7 | 12 | 536 |
| 10 | 120 | 0.75 | 0.353 | 2.421 | 5 | 6 | 280 |
| 11 | 120 | 0.25 | 0.262 | 1.852 | 2 | 4 | 304 |
| 12 | 180 | 0.75 | 0.302 | 2.230 | 4 | 5 | 244 |
| 13 | 60 | 0.25 | 0.385 | 2.993 | 6 | 8 | 423 |
| 14 | 10 | 0.50 | 0.505 | 3.562 | 6 | 15 | 468 |
| 15 | 10 | 0.75 | 0.525 | 3.961 | 8 | 12 | 533 |
| 16 | 10 | 0.25 | 0.498 | 3.719 | 7 | 14 | 593 |
| 17 | 180 | 0.25 | 0.187 | 0.503 | 0 | 1 | 142 |
| 18 | 180 | 0.50 | 0.182 | 0.445 | 0 | 1 | 178 |
| 19 | 20 | 0.50 | 0.491 | 3.402 | 4 | 16 | 444 |
| 20 | 20 | 0.05 | 0.577 | 4.238 | 11 | 15 | 617 |
| 21 | 180 | 0.05 | 0.502 | 3.886 | 6 | 11 | 528 |
| 22 | 20 | 0.25 | 0.472 | 3.605 | 10 | 14 | 563 |

TABLE 4-continued

Results for Deodorization of poultry litter

| | | | Pollutants | | | | |
|---|---|---|---|---|---|---|---|
| RUN | Time (mins) | Mass of Zeolite (g) | HCHO (mg/m$^3$) | TVOC (mg/m$^3$) | PM$_{2.5}$ (ug/m$^3$) | PM$_{10}$ (ug/m$^3$) | CO$_2$ (ppm) |
| 23 | 10 | 0.05 | 0.620 | 4.558 | 10 | 16 | 652 |
| 24 | 30 | 0.25 | 0.420 | 3.293 | 8 | 12 | 507 |

It is to be understood that the composition and method for waste treatment is not limited to the specific embodiments described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of forming a zeolite composition for waste treatment, the method comprising:
    refining kaolin to form a metakaolin;
    mixing the metakaolin with sodium hydroxide (NaOH) to obtain a mixture;
    aging and heating the mixture;
    washing the mixture;
    drying the mixture in a microwave to obtain crystals; and
    obtaining a zeolite composition.

2. The method of forming a zeolite composition for waste treatment as recited in claim 1, wherein the kaolin is Aloji Nigerian Kaolin.

3. The method of forming a zeolite composition for waste treatment as recited in claim 1, wherein the kaolin is refined at a temperature of about 600° C. to about 850° C.

4. The method of forming a zeolite composition for waste treatment as recited in claim 1, wherein a concentration of the NaOH comprises about 5 M to about 8 M.

5. The method of forming a zeolite composition for waste treatment as recited in claim 1, wherein the mixture is stirred with a magnetic stirrer for about 1 hour to about 3 hours.

6. The method of forming a zeolite composition for waste treatment as recited in claim 1, wherein the mixture is heated in an autoclave for about 3 hours.

7. The method of forming a zeolite composition for waste treatment as recited in claim 1, wherein the mixture is dried in a microwave at about 80° C. to about 150° C.

8. The method of forming the zeolite composition for waste treatment as recited in claim 1, wherein the mixture is dried in a microwave at 80° C., 115° C., or 150° C.

9. The method of forming a zeolite composition for waste treatment as recited in claim 1, wherein the mixture is dried in a microwave for about 8 hours.

10. A method of deodorizing animal waste, comprising the step of treating the animal waste with a crystalline zeolite composition produced according to the method of claim 1.

11. The method of deodorizing animal waste of claim 10, wherein the animal waste is poultry litter.

12. The method of deodorizing animal waste of claim 11, wherein a weight of the zeolite composition is between about 1% and about 15% by weight of the poultry litter.

13. The method of deodorizing animal waste of claim 12, wherein the weight of the zeolite composition is one of 1%, 5%, 10%, and 15% by weight of the poultry litter.

14. The method of deodorizing animal waste of claim 11, wherein the poultry litter is treated with the zeolite composition for from about 10 minutes to about 180 minutes.

15. The method of deodorizing animal waste of claim 14, wherein the poultry litter is treated with the zeolite composition for a time selected from the group consisting of about 10 minutes, about 20 minutes, about 30 minutes, about 60 minutes, about 120 minutes, and about 180 minutes.

16. The method of deodorizing animal waste of claim 11, wherein deodorizing the poultry litter comprises removing pollutants.

17. The method of deodorizing animal waste of claim 16, wherein the pollutants comprise one or more of formaldehyde (HCHO), total volatile organic compounds (TVOC), particulate matter, carbon dioxide (CO$_2$), and ammonia (NH$_3$).

18. The method of deodorizing animal waste of claim 17, wherein the particulate matter has a size of about 2.5 microns to about 10 microns.

19. The method of deodorizing animal waste of claim 18, wherein the particulate matter has a size of about 2.5 microns or about 10 microns.

* * * * *